(12) United States Patent
Eckmiller

(10) Patent No.: US 6,530,954 B1
(45) Date of Patent: Mar. 11, 2003

(54) ADAPTIVE SENSO-MOTOR ENCODER FOR NEUROPROSTHESES

(75) Inventor: Rolf Eckmiller, Bonn University (DE)

(73) Assignee: IIP Technologies GmbH, Bonn (DE)

(*) Notice: Subject to any disclaimer, the term of this patent is extended or adjusted under 35 U.S.C. 154(b) by 0 days.

(21) Appl. No.: 09/367,138

(22) PCT Filed: Feb. 20, 1998

(86) PCT No.: PCT/EP98/00971
§ 371 (c)(1),
(2), (4) Date: Feb. 29, 2000

(87) PCT Pub. No.: WO98/36793
PCT Pub. Date: Aug. 27, 1998

(30) Foreign Application Priority Data
Feb. 21, 1997 (DE) .......................................... 197 07 046

(51) Int. Cl.⁷ .............................. A61F 2/02; A61F 2/48; A61N 1/08
(52) U.S. Cl. ........................ 623/11.11; 623/24; 607/48; 607/60
(58) Field of Search ............................... 623/11.11, 24; 607/48, 60

(56) References Cited
PUBLICATIONS

R. Eckmiller, *Biology–Inspired Pulse Processing Neural Networks (BPN) for Neurotechnology*, vol. 2, Parts and 4, (May 1994).

Dagnelie & Massof, *Toward and Artificial Eye*, IEEE Spectrum, pp. 20–29 (May 1996).

R. Eckmiller, *Concerning the Development of Retina Implants with Neural Nets*, ICONIP'96—Hong Kong, pp. 21–28 (1996).

R. Eckmiller, *Neurotechnologie–Report* Mar. 31, 1995.

R. Eckmiller, *Neurotechnologie–Report* Apr. 16, 1994.

*Primary Examiner*—David J. Isabella
*Assistant Examiner*—A. Stewart
(74) *Attorney, Agent, or Firm*—Venable, LLP; Jeffrey W. Gluck; Robert Kinberg

(57) ABSTRACT

An adaptive sensory-motor encoder equipped with a central control unit for signal processing functions, monitoring functions, checking functions and/or external intervention functions. The encoder has a group of adaptive spatio-temporal filters for the purpose of converting sensor signals into stimulation pulse sequences, and it is equipped with an interface for coupling the encoder with an implantable microstructure for stimulation of nerve or glial tissue. The interface is executed in bi-directional design. Thus, along with control of nerve cells and administration of active substances, monitoring of sensor signals and biophysical parameters of spontaneous activity recorded at the implant site is also possible.

34 Claims, 5 Drawing Sheets

ADAPTIVE SENSO-MOTOR ENCODER FOR NEUROPROSTHESES

BACKGROUND OF THE INVENTION

1. Field of the Invention

The invention concerns an adaptive sensory-motor encoder as well as a spinal implant and a cranial implant.

2. Description of Related Art

There are several precursor systems of spinal implants known, that, for example, are employed in cases of transverse lesions of the spinal cord with paraplegia for control of urinary tract functions and for guidance of ambulating movements or grasping movements that work by means of stimulation contacts in the form of implants or that work transcutaneously (see Eckmiller and colleagues., Neurotechnology Report, 1994 and 1995).

The spinal implant precursors currently available or those in development have diverse limitations, for example, no adaptation, no functional increase of number of microcontacts and no bi-directional, perception-based control by the implant carrier.

In particular, the currently developed microcontact structures and signal and energy transfer systems operate unidirectionally from the external encoder to the implanted stimulator and therefore offer no possibility of ongoing monitoring of neural impulse activity of the stimulated neurons. Thus, the stimulation pulse sequence cannot be adapted to the spontaneous activity of the neurons. Furthermore, triggering of neurobiological impulses by stimulation pulses can not be monitored directly. Moreover, an assured impulse monitoring opportunity for possible temporal tuning and synchronization of the impulse sequences of multiple neurons is also lacking.

There are isolated rationales for development of implanted, active substance applicators that are controlled by need, for example for insulin, but there have been to date no cranial implants that have been successfully implemented. Cranial implants that, for example, are urgently needed for local, event-triggered administration of active substances for suppression of onset of epileptic events, are not available.

SUMMARY OF THE INVENTION

This invention undertakes to eliminate the foregoing problems and to create an adaptive, sensory-motor encoder, which with the aid of neural networks in dialogue with the implant carrier or in bi-directional signal and data exchange from implant and addressed nerve tissue, can perform an optimization of the perturbed nervous system functions, functionally increases the selectively reachable stimulation sites, and monitors the neural activity of individual neurons that are to be stimulated. The invention further seeks to create a process for the operation of an adaptive sensory-motor encoder, and further to provide a spinal implant and a cranial implant.

This problem is solved by an encoder with the characteristics described herein.

Because the encoder is bi-directionally coupled with implanted microcontacts, monitoring of the neural impulse activity of individual neurons to be stimulated and other signals and the execution of quasi-autonomous actions can be realized. The functions can be optimized either self-actuating by the neural network or in dialogue with the implant carrier. The number of the selectively addressable stimulation sites can be functionally increased and the neural activity of individual neurons monitored. The implanted structure can operate sensory-motor quasi-autonomously by using appropriate sensory and action components and an adaptive control system. Essential components and processes of the adaptive information processing system are implemented in various combinations, particularly for spinal implants in bi-directional contact with the spinal cord or the peripheral nervous system and for cranial implants in bi-directional contact with the structures of the central nervous system within the cranium.

Furthermore, for the first time an encoder is proposed that allows the number of selectively reachable stimulation sites to be functionally increased and also subsequently to adapt itself to new stimulation conditions. The encoder described herein can (on the basis of its structure and function as a group of adaptive spatio-temporal filters) in addition to the stimulation function, also perform monitoring an evaluation of the neural activity of the neurons to be stimulated.

The spatio-temporal filters associated with the individual microcontacts, to the extent possible, are tuned to optimum function individually in the dialogue between the encoder and the implant carrier.

In contrast with an encoder with static pre-processing; that is, without the possibility of individual adjustment, the present case allows, on the basis of the single relevant criterion; namely the specific functional enhancement of the given area of the nervous system, adjustment of the single spatio-temporal filters as separate encoder channels. This advantage includes the possibility that subsequent function changes, for example, as a result of shift of micro-contacts by corresponding adaptations of the spatio-temporal filter function, can be compensated for. An advantage of the tuning of the spatio-temporal filter function in the dialogue with the implant carrier or with an area of the carrier's nervous system is in the consideration of functional aspects, that only the actual implant carrier can incorporate into the optimization process and only in implicit form; namely, for example, by subjective assessment of his perception or by evaluation and function monitoring of his nervous system and their use in the encoder adjustment.

The asynchronous impulse sequences of the individual spatio-temporal filter outputs of the functionally separated encoder channels, as stimulation signals, selective stimulation sites are selectively tuned to one another in the dialogue with the implant carrier, in consideration of the of the neural impulses recorded at the stimulation site.

Because it is presumed that time courses and locale distributions of the stimulation signals that have been reciprocally tuned by superposition, have been suitably selected by an adaptation process and their field distributions effected at several microcontacts will, as stimulation foci, trigger local and temporal selective neural impulse excitations, the number of selectively addressable stimulation sites and their definition or cross-talk suppression will be functionally enhanced with fixed number of implanted microcontacts.

With a given, relatively low number of implanted and permanently functional microcontacts, whose position relative to the neurons can not be modified, it is of particular advantage, functionally; that is, by generation of suitable signals, to increase the number of selectively reachable stimulation sites or neurons and thus, at the same time, increase the number of separately accessible encoder channels with an adequate reserve of spatio-temporal filters. This advantage effects an improvement of the quality of the respective function.

The control or relief of defective functions of the spinal cord or peripheral nervous system with the aid of a partially implanted neuroprosthesis in the closest possible sensory and motor coupling with the implant carrier and by using quasi-autonomous sensory-motor functions of the implanted structure is thus made possible.

Using adaptive spinal implants the quality of the relief from functional impairments in the spinal cord or peripheral nervous system fundamentally improved and, with respect to diverse applications, is possible for the first time.

Alleviation of neural functional impairments of the central nervous system within the cranium is made possible, particularly for the purpose of reducing undesirable sensory, motor, or cognitive effects for a number of groups of neurological or psychiatric patients using an implanted structure with an active substance applicator and quasi-autonomous, sensory-motor functions in coupling with control and monitoring functions of the implant carrier.

For the first time, using adaptive cranial implants the quality of the relief of neural functional impairments in the central nervous system within the cranium is possible in diverse applications.

DESCRIPTION OF THE PREFERRED EMBODIMENT

Figure 1:
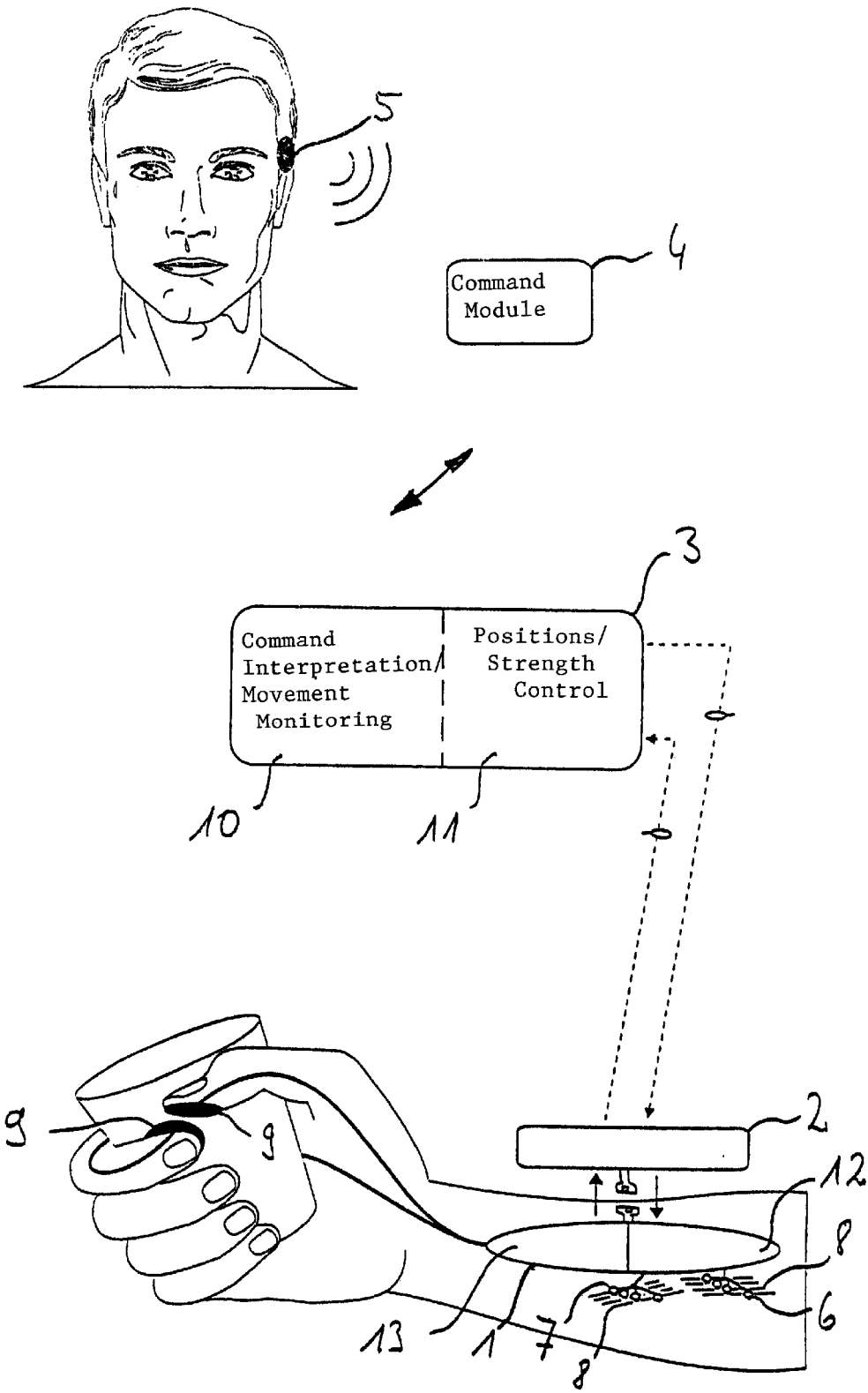
FIG. 1 is an example of a design form of a spinal implants in the area of the nerve tissue with a control unit and a command module activated by head movements.

A cranial implant used as a grasp prosthesis is illustrated in FIG. 1. This prosthesis is used when arm movements can still be performed in a paraplegic, but gripping movements with the hand are not possible.

The grasp prosthesis includes an implant (1) that communicates with a transcutaneous module (2). The module (2) is, in turn, in bi-directional wireless connection with an adaptive central control unit (3). The control unit receives commands from a command module (4) that is guided by a head movement sensor (5).

The implant (1) is in contact with nerve tissue (8) via micro-contacts (6, 7). In addition, several sensors (9), that pick up measurement values for the grip process in the area of the terminal thumb and one other finger, are connected to the implant (1).

The system described so far operates in the following manner to produce and control a grip process. Initially, the user moves the hand in the direction of an object that he intends to grasp. For example, the object can be a glass. When the hand is in the right position for grasping the glass, the grasp process is triggered by a particular head movement that is recognized by the head movement sensor (5). Then, the head movement sensor (5) communicates its signals to the command module (4). The command module (4) generates the appropriate control commands, which are then communicated to the control unit (3) either wirelessly or by signal conduction. The command interpreter (11), which also provides movement monitoring, is situated in an initial area (10) of the control unit (3). A second area (11) of the control unit (3) then issues positioning commands to the transcutaneous module (2), which then issues the command to the implant (1) and in particular to a stimulation unit (12) therein for stimulation of the appropriate neural pathways (8) via the micro-contacts (6, 7). The neural pathways (8) control the electrical stimulation of the hand muscles required for the grasping process, which then contract and trigger the grasping process.

The sensors (9) now detect the grip of the hand around the objects by picking up information regarding the position, the pressure applied, and slippage of the object. The goal of a grasp process is exertion of pressure that is as slight as possible in order not to damage the object (e.g., a raw egg), on the other hand, however, also to provide a grasp that is slippage free and so prevent dropping the object.

The sensor (9) signals are transferred to a sensor unit (13) of the implant (1). The signals received are transferred by the sensor unit (13) to the transcutaneous module (2), which then delivers the values determined after signal processing to the checking unit (11) of the control unit (3), where position and strength regulation for the grasping process is done. In the individual case, the stimulation of the nerve tract (8) via the micro-contacts (6) is guided in such a manner that an optimal grasp event results. The user can, for example, after grasping the glass, issue the information, by another head movement, to the head movement sensor (5) and thus to the command module (4) that the grasp process can now be sustained independently. The control unit (3) then effects the autonomous control of the grasp process. As an adaptive control unit (3) the stimulation is retro-coupled on a regular basis by way of the micro-contacts (6, 7) in the area of the nerve tract (8) in that the activity of the nerve tract (8) via the sensors (9) is picked up in the sensor unit (13) of the implant (1). The control unit (3) integrates this adaptability via a neural network that so regulates the site, the strength and the time course of stimulation of the nerve tract (8) that those nerve tracts are stimulated as precisely as possible and in the appropriate strength that is required for the grasp process. Thus, after an adaptive phase, an optimal grasp is possible.

Figure 2:
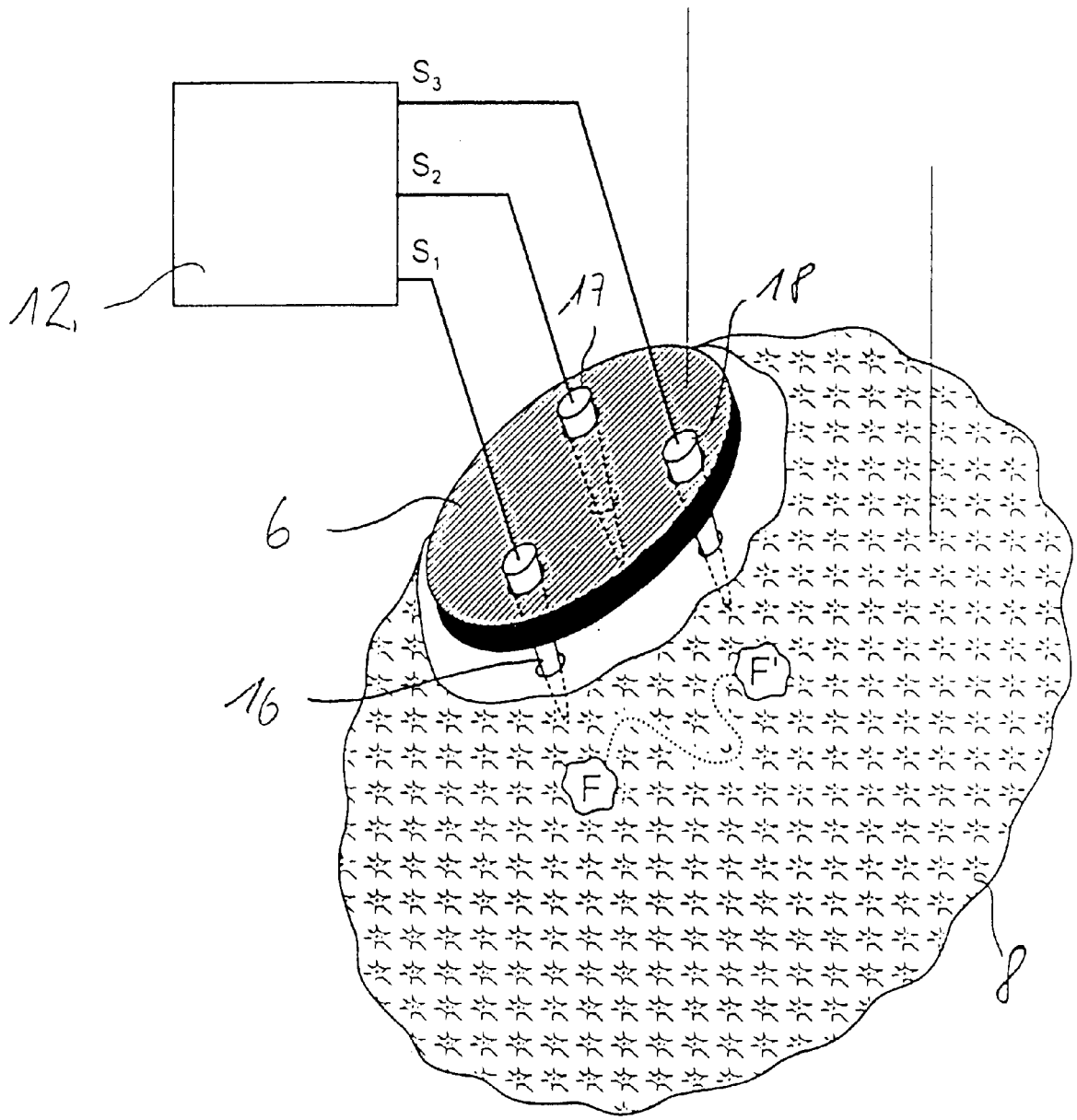
FIG. 2 is a schematic illustration of an implanted micro-contact structure for stimulation of nerve tissue not directly contacted.

FIG. 2 shows an illustrative example of micro-contacts (6) that impinge into nerve tissue (8). In the present example, three micro-contacts (16, 17, 18) are implanted into nerve tissue (8) and are positioned more or less randomly near certain nerve cells. The micro-contact structure (6, 16, 17, 18) is in each case essentially coarser than the matrix of the nerve cells (8). The micro-contacts (16, 17, 18) are supplied with signals (S1, S2, S3) via the stimulator (12).

In order to create a targeted neural stimulation, for example, a stimulation focus F must be attained that can not be directly affected by a micro-contact. The stimulation focus F can, however be attained, by conducting the signals (S1, S2, and S3) using different strengths, time courses and, above all, temporal intervals to the electrodes (16, 17, 18). The overlap of the signals generated can then be so arranged that the convergence of the signals in the area of the intended stimulation focus F exceeds the stimulation threshold of single or a few nerve cells, while the addition of signal progressions in the remaining area of the nerve tissue remains below the excitation threshold.

By changing the temporal sequence and the temporal signal progression of the various reciprocally tuned signals the stimulation focus can also be shifted from F to F'. For balancing of the stimulation functions that reach a stimulation focus which is not directly in conjunction with electrodes, an adaptive process is required. Since it is not exactly known which stimulation focus F, F' must be addressed for a particular neural stimulation, the adaptive sensory-motor control unit can offer only a certain signal pattern which the implant carrier then assess via a sensory perception or another sensor data evaluation. A second signal pattern, which is modified with respect to the first, is then likewise evaluated as to whether the intended neural stimulation is reached or not. The user needs only to say whether the later signal pattern better or worse suited is than the previous one. Using the check mechanism of a neural network and in the course of the checking process, an optimal signal time function is determined for the electrodes (16, 17, 18) for the purpose of excitation of the stimulation focus F.

Figure 3:
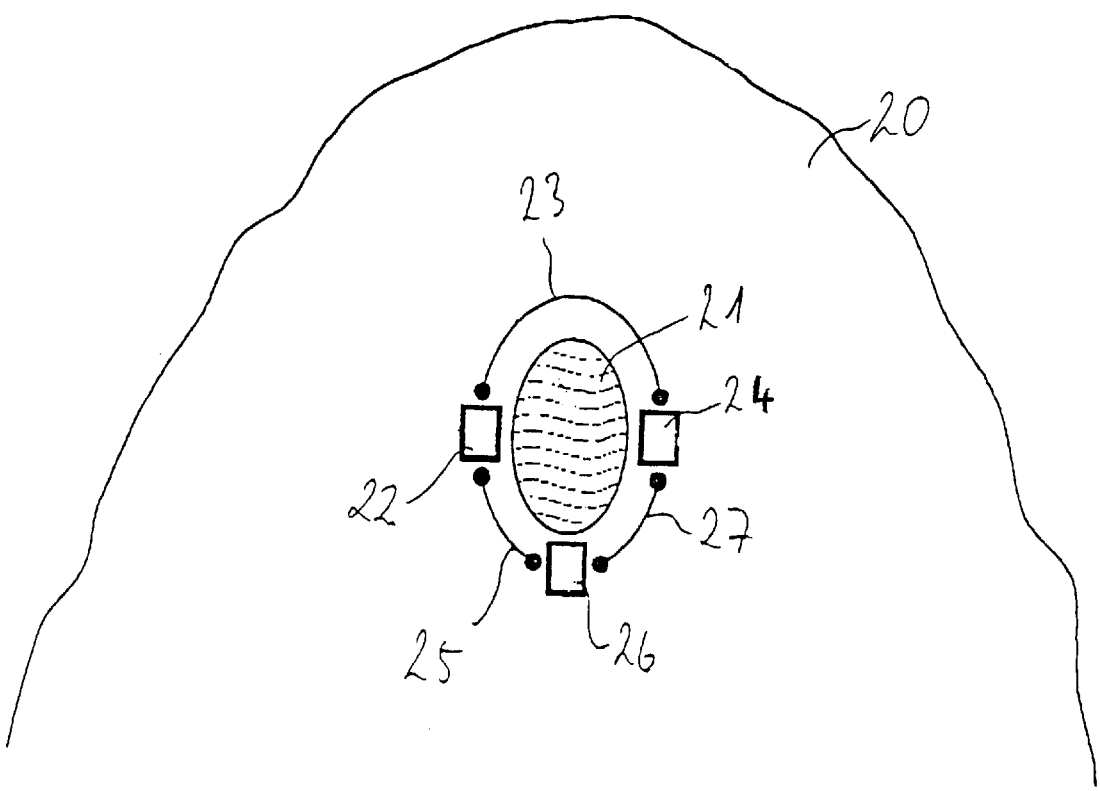
FIG. 3 is a schematic illustration of a cranial implant with the various modules in a block circuit diagram.

FIG. 3 depicts a cranial implant for monitoring and influencing a region of nerve tissue in the cortex. A neural tissue (20) that is to be monitored is provided with micro-contact (22) in the area of a region (21). The region (21) can, for example, be that region whose impaired function results in epileptic events. In such a case, a micro-contact structure (22) includes both the micro-contacts for stimulation of the nerve cells and also microsensors for monitoring the nerve cell activity and other biophysical parameters. The micro-contact structure (22) itself is connected to a signal path (23) with an adaptive processor (24) that has available to is a bi-directionally operating transmission and reception system. Otherwise, the micro-contact structure (22) is in contact with a signal tract (25) with an active substance reservoir (26). The active substance reservoir (26) is prepared for controlled local release of small quantities of an active substance, for example, in the nonliter range. Finally, the processor (24) is connected via another signal tract (27) directly to the active substance reservoir (26).

The three modules (22, 24, and 26) of the cranial implant function cooperatively to prevent epileptic events in the following way: The microsensors monitor the spontaneous nerve cell activity in the region (21) and communicate their measurement signals over the signal tract (23) to the processor (24) which then on the one hand evaluates the signals itself and, on the other hand, communicates a status report to an external encoder. With the occurrence of suspect characteristic nerve cell activity, which can, for example, be expressed in synchronous, neural activity within the region (21), the processor (24) identifies the existence of a stimulation pattern that can result in an epileptic event. It can then communicate on the one hand over the signal tract (23) stimulation pulse sequences to the micro-sensor (22), which counteract such synchronous, neural stimulation. When this purely electrical intervention is inadequate, the processor (24) can communicate an instruction over the signal tract (27) to the active substance reservoir (26). The reservoir administers a precisely metered dose of a pharmacological active substance, which in turn is capable of lowering the synchronous nerve cell activity to a normal level.

The type of control process, its temporal sequence, and the power of the respective effect on the nerve tissue region (21) by means of the micro-contact structure (22) and of the active substance reservoir is set and optimized at an external encoder, such that in the ideal scenario the patient is unaware of the artificial preventive intervention. In the case of physiological changes in the patient, the mode of action of the cranial implant is also further adapted. When this is done the encoder has the fundamental functions, that have already been described in connection with the design examples in FIG. 1 and FIG. 2.

Figure 4:
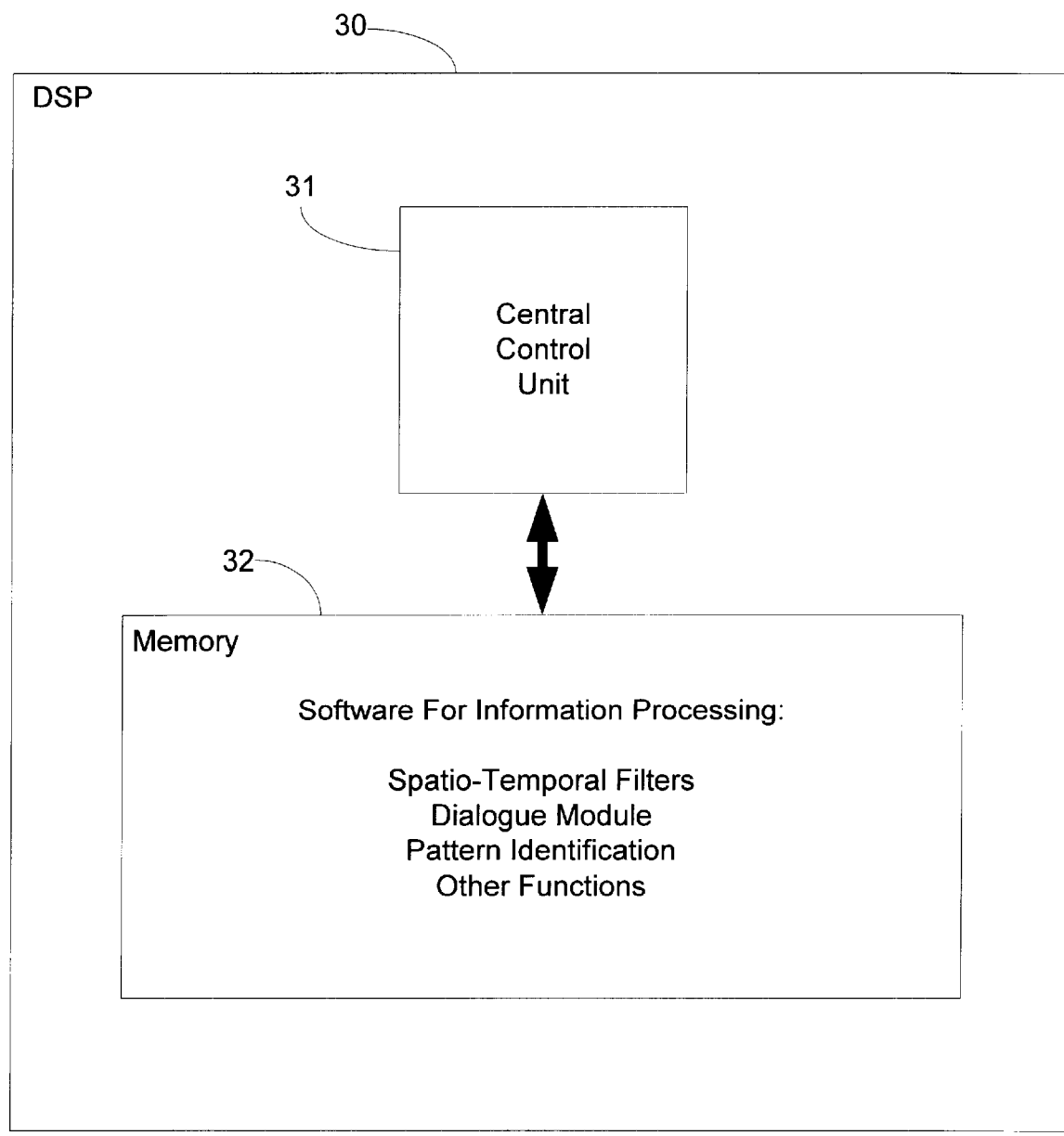
FIG. 4 shows a digital signal processor-based implementation of the encoder according to an embodiment of the invention.
Figure 5:
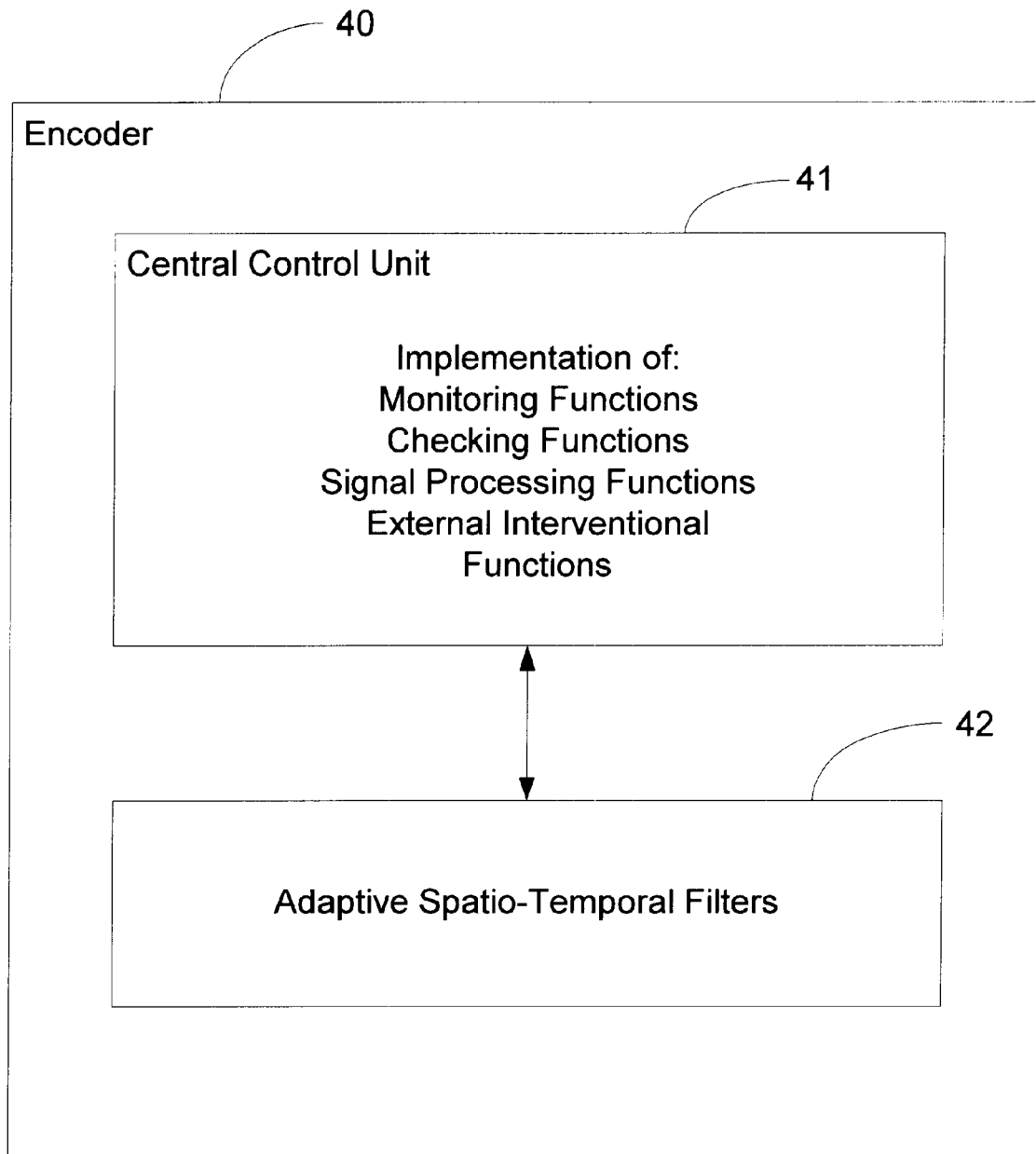
FIG. 5 shows an implementation of the encoder according to an embodiment of the invention.

An advantageous form of the structure and function of the encoders is shown in FIG. 4 and consists of a digital signal processor (DSP) (30), for example, the Texas Instruments C80 model, which is combined with a pre-processing module (not shown), a pulse signal emitter and receiver (not shown) for bi-directional communication with the evaluation input unit and the external monitoring and control (i.e., checking) system (not shown). The various adaptive information-processing functions are realized, particularly for spatio-temporal filters, dialogue module and pattern identification, in the DSP (30) with a central control unit (31). As is inherent in such DSPs, there is associated memory (32) that stores software implementing the various functions implemented by the DSP (30), the software being executed by central control unit (31) to implement its functions. The user receives, on the one hand, signals as stimulation pulses or sensory perceptions from the encoder and sends, on the other hand, the evaluation input of biophysical parameters and neural activity to the encoder. Furthermore, there is an exemplary form of the encoder in which the encoder, because of the bi-directional wireless signal and energy transfer, can be attached to the body or to a body-remote location. Further, an advantageous form of the encoder is where the spatio-temporal function space of the spatio-temporal filters for use an an encoder includes the information processing properties of the various classed of neurons contacted.

With the encoder, a direct communication is established with part of the nervous system that, on the one hand, is already spontaneously active. Thus, neural impulses from single neurons are generated without technical stimulation. For optimal adaptation to the stimulation pulse sequences to the respective spontaneous activity, for precise determination of the stimulation parameters for assured and, at the same time, biologically compatible 1:1 conversion of stimulation pulses into neural impulses, and for improved optimization of the temporal tuning and synchronization of the neural activity of several neurons, monitoring of the neural activity of single neurons to be stimulated is of considerable benefit.

With a design example of a process for adjustment of the spatio-temporal filters of the encoder in dialogue with the user the spatio-temporal filters are realized as spatio-temporal filters whose spatial and temporal function parameters are modified, within a sufficiently large functional space, in approximation of the respective information processing features of neurons; namely, by using externally accessible parameter exchange points placed at appropriate locations in the filter algorithm. An advantageous form of the adaptive process for the spatio-temporal filters is where a person, as a normal healthy person or as an implant carrier, in a perception-based dialogue with the encoder, the perceptual comparison between the desired pattern and the actual pattern; for example, by using as the evaluation input unit a row of several sliding controls or in the form of particular encoded head movements, communicates with a technical neural network with non-monitored adaptation rules and that the neural network establishes the next parameter vector for the spatio-temporal filters as well as the next desired value, with the goal of reducing the perceived pattern difference in the next dialogue step. An advantageous form of the search for the optimal parameter vectors for the spatio-temporal filters is where, in the dialogue module either from a neural network with non-monitored adaptation parameter vectors are produced that result in a particular perception for a given pattern presented and are correspondingly subjectively evaluated or, where in a dialogue module with another parameter adjusting system sequences of parameter vectors are used for the production of virtual motion in the function space of the spatio-temporal filters; for example, as continuous trajectories depending on the type of scanning or sweep processes, or as non-regular sequences, or as sequences of neurophysiological, particularly typical filter functions. In the course of this suitable timed sequence, the user casually reports the "sensible" perceptions produced by the collaboration of the given pattern, the pre-processing module, the following spatio-temporal filters and that part of the nervous system coupled to the associated micro-contact and, then, in the region of the function space determined in this process, a more precise parameter optimization can be undertaken based on perception.

An exemplary form of the generation of asynchronous impulse sequences is where the output signals of the individual spatio-temporal filters are transformed into asynchronous impulse sequence, relevant to the activity of the neurons, by using suitable convert algorithms of the quasi-continuous time functions of the spatio-temporal filters and where impulse sequence—time courses and points in time of the occurrence of single impulses can be shifted in the dialogue phase by using variable time delay elements.

An exemplary form of the process for temporal coupling of the asynchronous impulse sequences generated by several spatio-temporal filters of the encoders for the purposes of triggering nerve cell impulses is where the-transmission time point of the individual impulse signals are varied by controllable time delay elements in such a way that temporal coupling up to precise asynchronous occurrence results, wherein the variation of the time delay is regulated by the implant carrier. Or, in the dialogue this occurs based on perception via a neural network, or is externally regulated, in that the selection of the impulse groups that are to be temporally coupled can take into consideration the impulses coming both from the spatio-temporal filters and those recorded in the interface and that in view of the very different momentary impulse rates of the different spatio-temporal filters, suitable criteria are established for inclusion of individual impulses in the impulse groups that are to be coupled.

An exemplary example of the process for functional increase of the number and definition of the selectively addressable stimulation sites in the case of a given number of stationary implanted micro-contacts is where the impulse signals from a given spatio-temporal filter are conducted to several, locally adjacent micro-contacts, whereby the characteristic time courses—that have been established for each micro-contacts and corresponding to current amplitude, polarity, and phase length in the interface—of the electro-magnetic field in the area of the neurons to be stimulated have the effect that said stimulation signals, which have been tuned to each other by superpositioning, trigger locally and temporally selective neural impulse excitations in the field distributions at several micro-contacts and that the selective stimulation sites can be rapidly changed by suitable variation of the superpositioned stimulation signals and that the respective variation of diverse parameters of the reciprocally tuned stimulation signals results in the perception-based dialogue with the implant carrier via a neural network, or other signal variation process for the determination of as many as possible simulation sites leading to selective and defined neural excitation. Further, this advantageous form consists in the optimization of the stimulation-time functions is improved with respect to intended single cell selectivity and lasting biocompatibility through the comparison of recorded neural impulses to the stimulation signals.

A exemplary form of the monitoring system for a partially sensory-motor autonomously functioning implanted structure of the encoder is where the implanted micro-contacts are used both for stimulation and for recording of neural impulses, in that the recorded impulses and other physical or chemical signals from the implanted structure are reported through suitable pre-amplifiers and optical or electromagnetic transmitters to the encoder and there, the recorded neural signals are further processed for the various purposes of the encoder function.

An exemplary form of the partially autonomous sensory-motor actions of the implanted structure is where, by the use of various sensors accessible in the implanted structure that detect physical or chemical values, or using various actors such as, for example, electrical stimulation electrodes, mechanical micro-actors, chemical active substance applicators, or thermally acting probes for healing or micro-surgical purposes, structures for the performance of chemical analysis and processes within the implanted structure and using a partially neural, adaptive control system in communication with the encoder, quasi-autonomous, diverse sensory-motor actions can be executed, for example, rapid response effects on the local tissue can be executed in response to the sensory data just detected. In this case, the bi-directional coupling with the encoder can be used as control or checking.

An exemplary form of the adaptive spinal implant, for example for use in paraplegics for neural modulation of the urinary tract, for guidance of the grip or walking movements, or for the reduction of phantom pain following amputation is where the implanted microstructure is situated in the spinal cord, the peripheral nervous system, or in muscle groups, whereby the external adaptive encoder in bi-directional communication with the implanted structure is carried on the body of the user as a portable unit and is in bi-directional communication with the user for signal reception and functions to a large degree autonomously or can be controlled by the user through manipulation or, for example, through head or eye movements. An exemplary form of the implanted structure is where quasi-autonomous sensory-motor actions such as, for example, a need-driven administration of growth hormone or thermal effects are performed.

An exemplary form of the adaptive cranial implant, for example, as need-triggered local administration of active substance for epileptic patients, parkinsonism patients, or psychiatric patients, is where the implanted structure—including local detectors of physical, neurophysiological and ionic, molecular, and active substance concentrations, and also active substance depots with the possibility of simple external replenishment, local active substance dosers with control and adaptive information processing module—is situated intracranially and communicates bi-directional with an external encoder, whereby a medically and technically specially qualified team, after informed consent of the patient, similar to, for example, prior to the decision regarding micro-surgical intervention by using implanted thermally acting probes, not only monitors but also checks the individual functions and that the individual functions of the patients in perception-based dialogue can be optimized and, monitored. An exemplary example of the implanted structure is where the quasi-autonomous sensory-motor actions, such as, for example, need-driven administration of growth hormone or locally deficient neurotransmitter for synaptic functions; in other words, the biological contacts between nerve cells that are fundamentally involved in learning and adaptation and, for example, the need-driven suppression of epileptic events or thermal effects are effected.

I claim:

1. An adaptive sensory-motor encoder for use as a neuroprosthesis in the central nervous system within the cranium or the spinal cord or within the peripheral nervous system, said encoder comprising:

a central control unit, the central control unit carrying out at least one of signal processing functions, monitoring functions, checking functions, and external interventional functions, the central control unit being in bi-directional communication with a microstructure capable of being implanted for at least one of stimulation of nerve or glial tissue and monitoring of brain or other neural functions, said bi-directional communication being carried out through a bi-directional interface coupling said microstructure with the encoder; and at least two adaptive spatio-temporal filters, the spatio-temporal filters carrying out at least one of sensory or motor stimulation functions and monitoring functions.

2. The encoder according to claim 1, wherein said microstructure is operated in at least a quasi-autonomous fashion, under the control of said central control unit, and wherein said central control unit comprises an adaptive control unit.

3. The encoder according to claim 1, further comprising: means for transmitting signals directing that a substance or a form of energy be applied, under control of said checking function.

4. The encoder according to claim 1, further comprising: means for receiving signals indicative of at least one of neural or glial activity and ionic, molecular, or active substance concentration, as part of said monitoring functions.

5. The encoder according to claim 4, wherein said monitoring functions receive said signals from a monitoring system included in said microstructure.

6. A neuroprosthesis capable of being used in the central nervous system within the cranium or the spinal cord or within the peripheral nervous system, comprising:

an adaptive sensory-motor encoder comprising:

a central control unit, the central control unit carrying out at least one of signal processing functions, monitoring functions, checking functions, and external interventional functions; and at least two adaptive spatio-temporal filters, the spatio-temporal filters carrying out at least one of sensory or motor stimulation functions and monitoring functions;

a microstructure capable of being implanted for at least one of stimulation of nerve or glial tissue and monitoring of brain or other neural functions; and a bi-directional interface for coupling the implanted microstructure with the encoder.

7. The neuroprosthesis according to claim 6, wherein said microstructure is operated in at least a quasi-autonomous fashion, under the control of said central control unit, and wherein said central control unit comprises an adaptive control unit.

8. The neuroprosthesis according to claim 6, wherein said encoder further comprises:

means for transmitting signals directing that a substance or a form of energy be applied, under control of said checking function.

9. The neuroprosthesis according to claim 6, wherein said encoder further comprises:

means for receiving signals indicative of at least one of neural or glial activity and ionic, molecular, or active substance concentration, as part of said monitoring functions.

10. The neuroprosthesis according to claim 6, wherein said microstructure includes at least two micro-contacts capable of being implanted in a stationary fashion, the micro-contacts for at least one of conducting stimulation signals to and monitoring signals from nerve or glial tissue in which they are implanted.

11. The neuroprosthesis according to claim 10, wherein said stimulation signals comprise impulse signals, and the impulse signals are conducted to nerve or glial tissue via either one or more than one of said micro-contacts.

12. The neuroprosthesis according to claim 6, wherein said encoder determines, by means of an adaptive process, time courses and local distributions of stimulation signals, to trigger local and temporally selective stimulation.

13. The neuroprosthesis according to claim 6, wherein said microstructure includes a monitoring system in bi-directional communication with said encoder, the monitoring system monitoring and evaluating recorded signals and controlling effects elicited by said microstructure.

14. The neuroprosthesis according to claim 13, wherein said monitoring system comprises:

at least one sensor for sensing at least one of mechanical, electrical, and chemical phenomena;

means capable of eliciting at least one of physical and chemical local effects at an implant site; and an adaptive sensory-motor checking system in communication with said encoder.

15. The neuroprosthesis according to claim 14, wherein signals from said at least one sensor are transmitted to said encoder by said adaptive sensory-motor checking system, via said bi-directional interface, for further processing by said encoder, wherein said signals are made externally accessible.

16. The neuroprosthesis according to claim 15, wherein a signal transmission path from said at least one sensor to said encoder and including said adaptive sensory-motor checking system and said bi-directional interface includes at least one of: a signal transformer, a pre-amplifier, and a transmitter.

17. The neuroprosthesis according to claim 6, wherein said microstructure includes at least two bi-directional micro-contacts capable of being implanted, the bi-directional micro-contacts for conducting stimulation signals to nerve or glial tissue in which they are implanted and for detecting at least one physical or chemical phenomenon.

18. The neuroprosthesis according to claim 17, wherein said microstructure further comprises at least one additional micro-contact for detecting at least one physical or chemical phenomenon.

19. The neuroprosthesis according to claim 6, further comprising:

a perception evaluation system for optimizing function of the neuroprosthesis, the perception evaluation system interacting with said encoder.

20. The neuroprosthesis according to claim 19, wherein said perception evaluation system includes a neural network.

21. The neuroprosthesis according to claim 19, wherein said perception evaluation system includes means for inputting perception-related information by a human observer.

22. The neuroprosthesis according to claim 21, wherein said human observer is a person in whom said neuroprosthesis is implanted.

23. The neuroprosthesis according to claim 6, wherein said microstructure includes a local adaptive checking system that performs partially automatic evaluation of signals recorded at a site in which said microstructure is implanted and that converts said signals into local action commands.

24. An adaptive spinal implant for alleviation of neural functional impairment in the spinal cord or peripheral nervous system, comprising:

an adaptive encoder;

a sensory-motor structure capable of being implanted and that functions in a quasi-autonomous fashion; and a bi-directional signal and energy transfer system, wherein the structure capable of being implanted and the transfer system function so as to facilitate bi-directional contact between the encoder and parts of at least one of the spinal cord, the peripheral nervous system, and a muscle group.

25. An adaptive cranial implant apparatus for alleviation of neural functional impairments of the central nervous system, comprising:

an adaptive encoder that includes:

a central control unit, the central control unit performing at least one of signal processing functions, monitoring functions, checking functions, and external intervention functions;

a structure capable of being implanted, functioning in quasi-autonomous fashion, and which may also receive control inputs from the adaptive encoder, comprising:

at least two microcontacts;

at least two detectors;

at least one active substance depot; and means for administering the active substance from the active substance depot; and a signal and energy transfer system for facilitating bi-directional contact between the adaptive encoder and the structure capable of being implanted, and thus with the brain.

26. The adaptive cranial implant apparatus according to claim 25, the structure capable of being implanted further comprising:

a quasi-autonomous monitoring system that evaluates signals detected by at least one of the detectors by using a local adaptive checking system and converts them into at least one of physical or chemical local action commands.

27. The adaptive cranial implant apparatus according to claim 26, wherein administration of an active substance from the at least one active substance depot is controlled in dependence on a pathophysiological condition or status space by the quasi-autonomous monitoring system.

28. The adaptive cranial implant apparatus according to claim 27, further comprising:

means for direct control by at least one of an implant carrier and a person other than an implant carrier, wherein the administration of an active substance is also controlled via at least one of the encoder and the implant carrier or other person via the means for direct control.

29. The adaptive cranial implant apparatus according to claim 25, wherein the encoder functions to perform perception-based, automatic or externally-checked function adaptation, and further comprising:

sensory spatio-temporal filters for sensation optimization; and motor adaptive modules for optimization of progress of movement, need-driven administration of active substances, or micro-surgical or curative effects.

30. The adaptive cranial implant apparatus according to claim 29, wherein the motor adaptive modules comprise motor spatio-temporal filters.

31. The adaptive cranial implant apparatus according to claim 25, further comprising:

a detection system for detecting at least one of head movements, eye movements, and other movements, the detection system being coupled to the encoder, where the detected movements are capable of being used for communicating at least one of intentions and perceptions of a person in whom the apparatus has been implanted to the encoder.

32. The adaptive cranial implant apparatus according to claim 31, wherein the perceptions of the person in whom the apparatus has been implanted are used for purposes of at least one of monitoring, controlling, and optimizing function of the apparatus.

33. The adaptive cranial implant apparatus according to claim 31, further comprising:

a portable command input unit through which the detection system communicates the at least one of intentions and perceptions to the encoder.

34. The adaptive cranial implant apparatus according to claim 25, further comprising:

a manual input unit coupled to the encoder, whereby a person inputs information for use in at least one of adapting and optimizing the function of the apparatus.

* * * * *